US009000770B2

(12) United States Patent
Chen et al.

(10) Patent No.: US 9,000,770 B2
(45) Date of Patent: Apr. 7, 2015

(54) ELECTROCHEMICAL BLOOD TEST STRIPS AND DIAGNOSIS SYSTEMS USING THE SAME

(75) Inventors: Sz-Hau Chen, Taipei (TW); Yi-Chen Lu, Hsinchu (TW); Chun-Yi Yen, Taichung (TW)

(73) Assignee: Apex Biotechnology Corp., Hsinchu (TW)

( * ) Notice: Subject to any disclaimer, the term of this patent is extended or adjusted under 35 U.S.C. 154(b) by 190 days.

(21) Appl. No.: 13/530,868

(22) Filed: Jun. 22, 2012

(65) Prior Publication Data

US 2013/0118899 A1 May 16, 2013

(30) Foreign Application Priority Data

Nov. 15, 2011 (TW) ............... 100141576 A

(51) Int. Cl.
*G01N 27/02* (2006.01)
*G01N 33/86* (2006.01)
*G01N 27/28* (2006.01)
*G01N 27/327* (2006.01)

(52) U.S. Cl.
CPC ................... *G01N 27/3272* (2013.01)

(58) Field of Classification Search
CPC .......... G01N 27/3274; G01N 33/4905; G01N 27/3272; B01L 2300/0825; B01L 2300/087; B32B 1/00; B32B 1/2457; B32B 1/208

USPC ................... 219/201–208, 482–506; 422/73; 204/403.01; 436/70
See application file for complete search history.

(56) References Cited

U.S. PATENT DOCUMENTS

| | | | |
|---|---|---|---|
| 2005/0230252 A1* | 10/2005 | Tsai et al. ................... 204/450 |
| 2007/0144918 A1* | 6/2007 | Hsu et al. ................... 205/775 |
| 2008/0164142 A1* | 7/2008 | Alvarez-Icaza et al. ...... 204/164 |
| 2008/0297169 A1* | 12/2008 | Greenquist et al. ........... 324/600 |
| 2013/0270113 A1* | 10/2013 | Huang ..................... 204/403.02 |

FOREIGN PATENT DOCUMENTS

| | | |
|---|---|---|
| TW | 200942619 | 10/2009 |
| TW | M378382 | 4/2010 |
| TW | 201132975 | 10/2011 |

* cited by examiner

*Primary Examiner* — Alex Noguerola
(74) *Attorney, Agent, or Firm* — Liu & Liu

(57) ABSTRACT

Electrochemical blood test strips and diagnosis systems are presented. An electrochemical blood test strip for measuring HCT% and prothrombin time includes an electrode plate having electrode circuit patterns on an insulator substrate; a separation plate disposed on the electrode plate defining a blood sample region, a channel and three reaction regions; and a cover plate disposed on the separation plate having a blood sample inlet and vents. In measuring, one of the three reaction regions is used for detecting hemoglobin and hematocrit and the other two reaction regions are biochemical reaction regions and used for detecting prothrombin time.

10 Claims, 5 Drawing Sheets

ELECTROCHEMICAL BLOOD TEST STRIPS AND DIAGNOSIS SYSTEMS USING THE SAME

CROSS REFERENCE TO RELATED APPLICATIONS

This application claims the right of priority based on Taiwan Patent Application No. 100141576 entitled "ELECTROCHEMICAL BLOOD TEST STRIPS AND DIAGNOSIS SYSTEMS USING THE SAME", filed on Nov. 15, 2011, which is incorporated herein with reference and assigned to the assignee herein.

FIELD OF THE INVENTION

The present invention relates to electrochemical blood test strips, and more particularly, to electrochemical blood test strips and diagnosis system for measuring hemoglobin, prothrombin time and hematocrit (HCT).

BACKGROUND OF THE INVENTION

Two pathways or coagulation cascades, known as the intrinsic and extrinsic pathways, lead to the formation of a clot. When a human body is injured, the extrinsic pathway is first triggered to control the in vivo coagulation. In addition to a blood sample, the coagulation reaction needs some additional tissue factors. The inactive factor X is catalyzed into factor Xa. The prothrombin (factor II) can be transformed from the factor Xa to the thrombin (factor IIa) by the effects of factor Va, acidic phospholipids and calcium ions. The thrombin then transforms fibrinogen into fibrin, enhancing the platelet of the endothelial cells gathered at injury. The thrombin can also enhance the role of factor XIII, linking each fibrous protein molecule to a stable fibrin. Therefore, inspecting the prothrombin time would not only determine whether the function of external activation factor of the coagulation system is normal, but also assess and monitor oral anticoagulants treatment, liver function, vitamin K deficiency, coagulation factor deficiency, and disseminated intravascular coagulation (DIC) syndrome.

Some prior art relating electrochemical blood test strips, such as U.S. Pat. No. 7,674,616, the entirety of which is hereby incorporated by reference, disclose a coagulation inspection device with automatically collecting blood samples. The coagulation inspection device determines the coagulation time by measuring capacitance or impedance changes between two electrodes. These technologies may, therefore, improve the simplicity of detection but cannot achieve the high precision and accuracy that the optical detection methods would achieve.

Accordingly, new electrochemical blood test strip and diagnosis system are needed for measuring prothrombin time and HCT with a shortened test time, simplicity and high accuracy.

SUMMARY OF THE INVENTION

One aspect of the present invention is to provide an electrochemical blood test strip for measuring hemoglobin, prothrombin time and hematocrit (HCT) respectively.

Another aspect of the present invention is to provide a diagnosis system using the electrochemical blood test strip. The diagnosis system exhibits with the function of calibration and compensation, provides an accurate analysis of the blood characteristics, reduces the chance of a test error, and improves the measurement accuracy.

According to an embodiment of the invention, an electrochemical blood test strip, comprising: an electrode plate having circuit of measuring electrode pattern on an insulator substrate; a separation plate disposed on the electrode plate defining a blood sample region, a channel and three reaction regions; and a cover plate disposed on the separation plate having a blood sample inlet and vents, wherein in measuring, a first reaction region is used for detecting hemoglobin and hematocrit and a second and a third reaction regions are biochemical reaction regions and are used for detecting prothrombin time.

In another embodiment, an electrochemical blood test strip, comprising: a blood sample region for accommodating tested blood sample; a first reaction region used for detecting hemoglobin and hematocrit; a second and a third reaction regions, which are biochemical reaction regions used for detecting prothrombin time; and a channel, wherein the blood sample region is connected to the three reaction regions by the channel, and wherein the channel includes a branch such that the distance between the blood sample region and the second reaction region and the distance between the blood sample region and the third reaction region are the same.

According to further another embodiment of the invention, a diagnostic device using the electrochemical blood test strip, the diagnostic device comprises: a test strip receiving unit for accommodating the electrochemical blood test strip; an AC generation unit for providing an alternating current with predetermined frequency and voltage to the electrochemical blood test strip; a signal receiving unit to retrieve a response signal from the electrochemical blood test strip; a microprocessor for calculating the response signal and rendering results of the HCT and the prothrombin time; and a display unit for displaying inspected results of the HCT and the prothrombin time from the microprocessor.

BRIEF DESCRIPTION OF THE PICTURES

The foregoing aspects and many of the attendant advantages of this invention will become more readily appreciated by reference to the following detailed description, when taken in conjunction with the accompanying pictures, wherein.

Figure 2A:
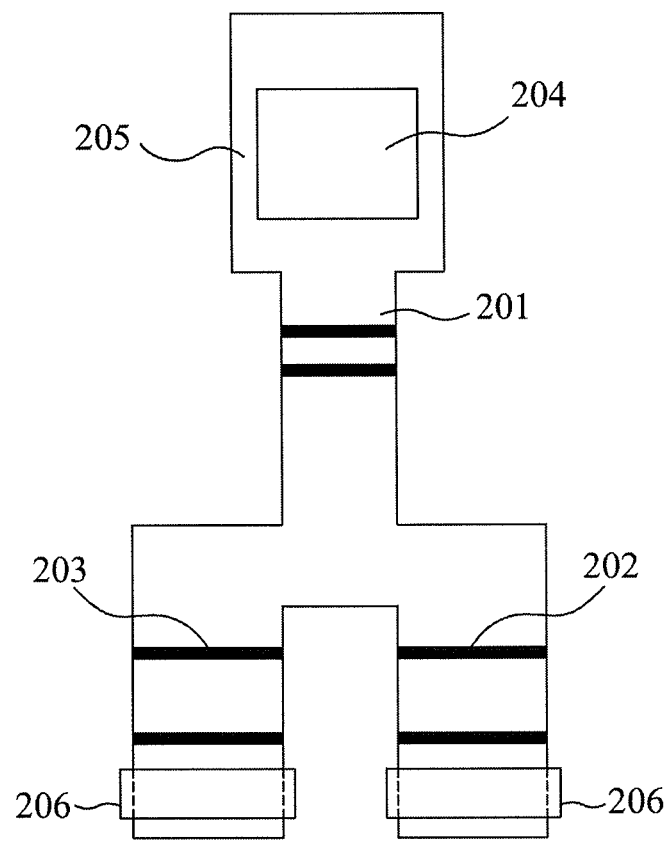
Figure 2B:
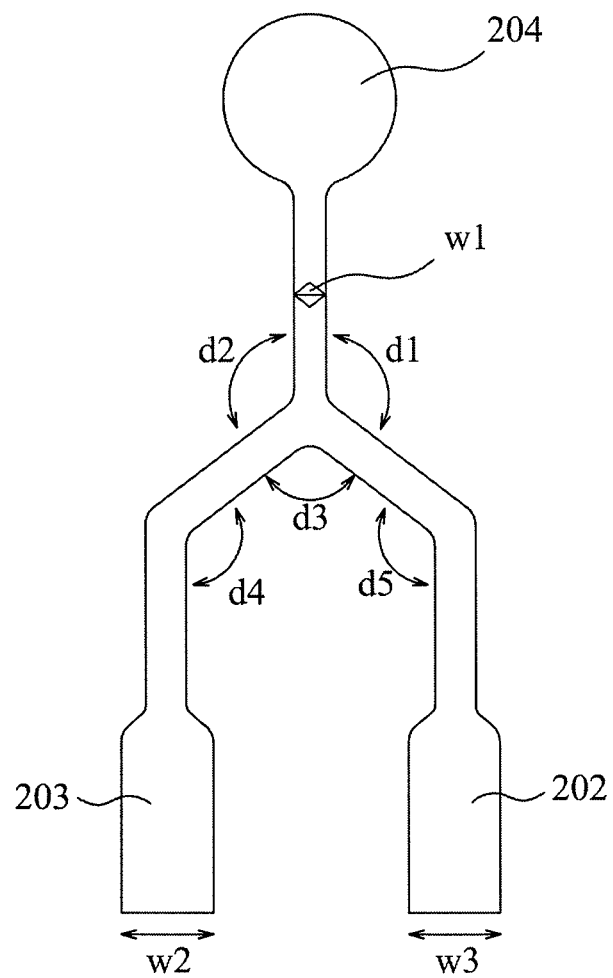
Figure 3:
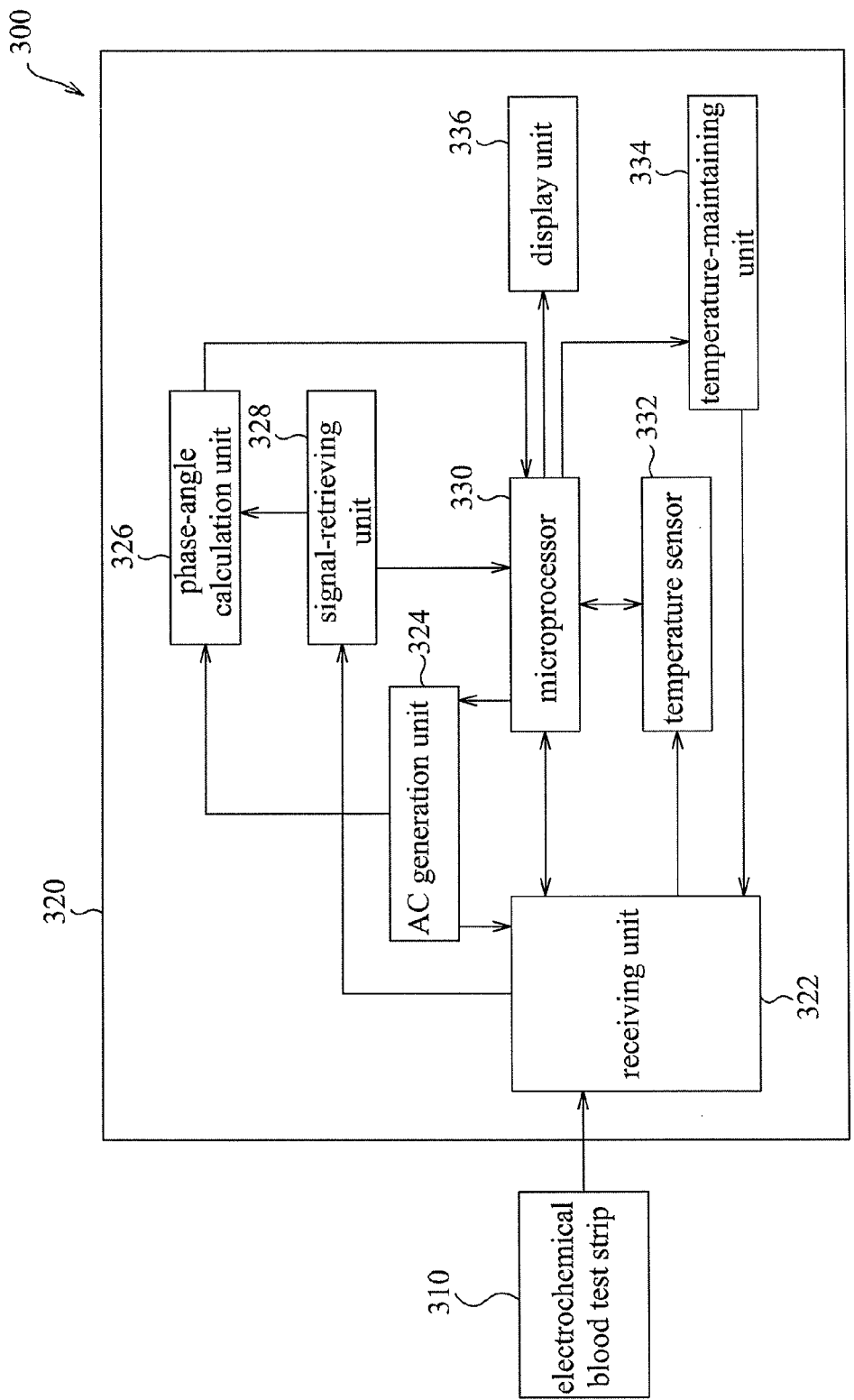

FIG. 2A schematically illustrates the blood sample region, the channel and three reaction regions of the electrochemical blood test strip in accordance with some embodiments of the present invention;

FIG. 2B schematically illustrates the relationship between the channel width and the inflected angle of the electrochemical blood test strip in accordance with other embodiments of the invention; and FIG. 3 is a schematic view of an exemplary diagnostic device for measuring prothrombin time and HCT in accordance with some embodiments of the present invention.

DETAILED DESCRIPTION OF THE INVENTION

Reference will now be made in detail to several exemplary embodiments of the invention, examples of which are illustrated in the accompanying drawings. Wherever possible, the same reference numbers are used in the drawings and the description to refer to the same or like parts. In the drawings, the shape and thickness of an embodiment may be exaggerated for clarity and convenience. This description will be directed in particular to elements forming part of, or cooperating more directly with, apparatus in accordance with the present invention. It is to be understood that elements not specifically shown or described may take various forms well known to those skilled in the art. Further, when a layer is referred to as being on another layer or "on" a substrate, it may be directly on the other layer or on the substrate, or intervening layers may also be presented.

Some exemplary embodiments of the present invention will now be described in greater details by referring to the drawings that accompany the present application. It should be noted that the features illustrated in the drawings are not necessarily drawn to scale. Descriptions of well-known components, materials, and process techniques may be omitted so as to not unnecessarily obscure the embodiments of the invention. Any devices, components, materials, and steps described in the embodiments are only for illustration and not intended to limit the scope of the present invention.

In view of the aforementioned problems, the following embodiments provide a diagnosis system for measuring prothrombin time and hematocrit (HCT) of blood test. More specifically, the diagnosis system may be used to improve the characteristics contained in electrochemical blood test strips and measurement accuracy. Measurement for blood coagulation or HCT may be more suitably used in quantitative analysis of prothrombin time (i.e., clotting time). As used herein, the term "hematocrit" refers to the percentage of packed red blood cells in a volume of whole blood.

Figure 1A:
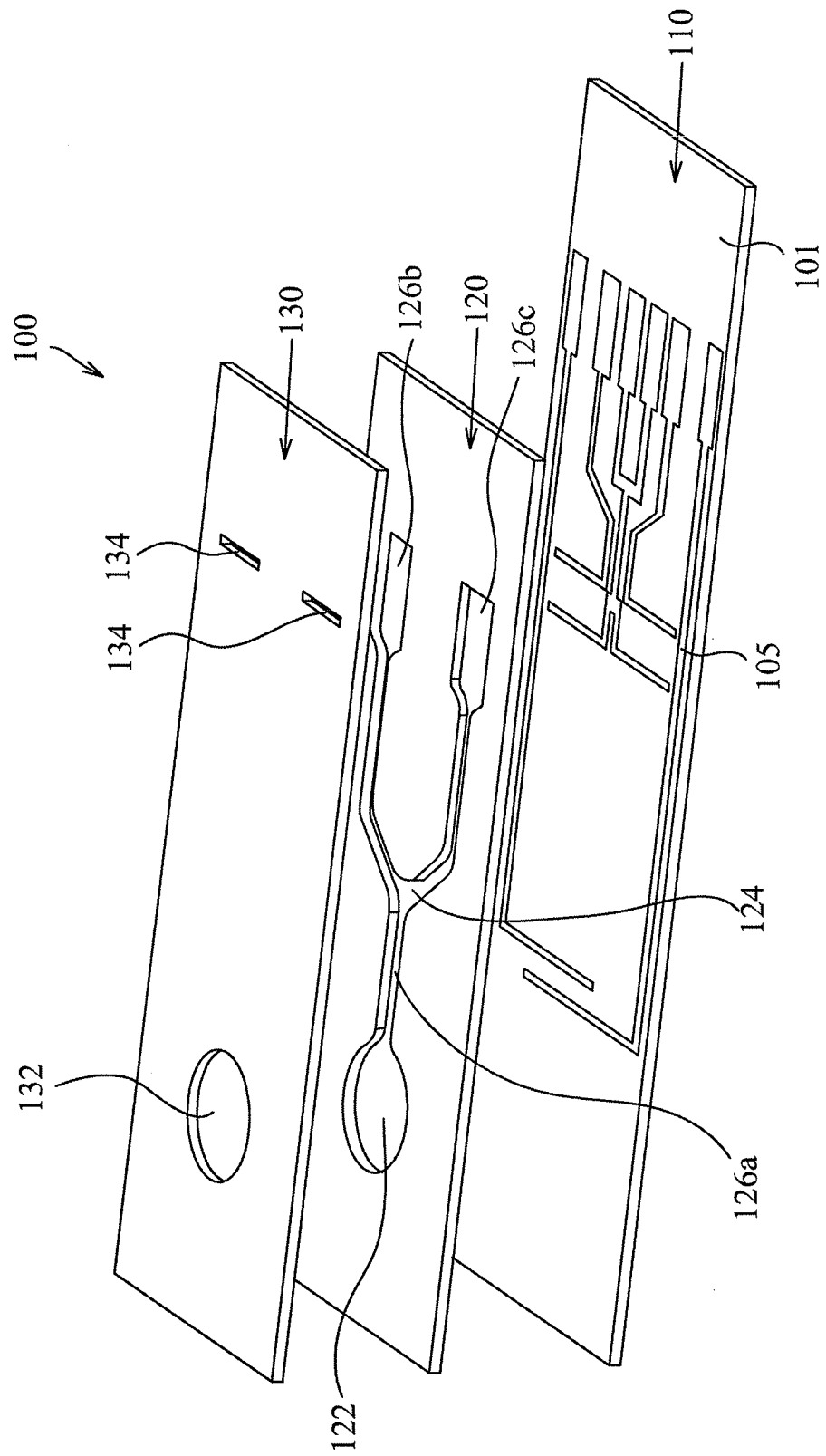
FIG. 1A illustrates an explosive view of an electrochemical blood test strip in accordance with one embodiment of the present invention.

FIG. 1A illustrates an explosive view of an electrochemical blood test strip in accordance with one embodiment of the present invention wherein the broken line indicates the relative positions between various elements. The electrochemical blood test strip 100 includes an electrode plate 110 having circuit of measuring electrode pattern 105 on an insulator substrate 101. A separation plate 120 is disposed on the electrode plate 110 defining a blood sample region 122, a channel 124 and three reaction regions 126a, 126b and 126c. The blood sample region 122 is connected to the three reaction regions 126a, 126b and 126c by the channel 124. The channel 124 includes a branch such that the distance between the blood sample region 122 and the second reaction region 126b and the distance between the blood sample region 122 and the third reaction region 126c are the same. A cover plate 130 is disposed on the separation plate 120 having a blood sample inlet 132 and vents 134.

The insulator substrate 101 is electrically insulating, and its material may include but is not limited to a base plate composed of porous materials. In one embodiment, the base plate of the electrochemical blood test strip includes pores with diameters in a range of about 0.1 µm to about 100 µm. The circuit of measuring electrode pattern 105 may be made with any conductive materials. For example, the measuring electrode pattern 105 is a stacked structure comprising a metal base layer, a metal adhesive layer and a surface metal layer (not shown). It should be noted that the measuring electrode pattern 105 is not limited the above-mentioned three-layered structure, it can alternatively or optionally be a single-layered structure or a dual-layered structure with a metal adhesive layer and a surface metal layer.

The metal base layer can be formed by metal deposition and lithography and etching resulting in metal circuit disposed on the insulator substrate. The metal base layer can be made of Cu, Al, Fe, Ag, W, and alloys thereof. The metal adhesive layer is used for combining the metal base layer and the surface metal layer and can serve as a barrier layer preventing inter-diffusion between the metal base layer and the metal adhesive layer. The metal adhesive layer can act as anti-corrosion layer and anti-oxidization layer to prevent the surface metal layer from oxidization. The metal adhesive layer can be made of Ni, Co, Sn, Zn, and alloys thereof. The surface metal layer can be made of Au, Pd, Pt, Rh, Ru, Cu, Sn, W, Ti, and alloys thereof. The metal adhesive layer and the surface metal layer can be formed by chemical plating techniques. For example, metal ions in the solution can be replaced with the material of the coating surface by the metal precipitation. In one embodiment, the electrode plate 110 is performed by hydrophilic treatment resulting in surface hydrophilicity such as by rinsing with surfactants.

Figure 1B:
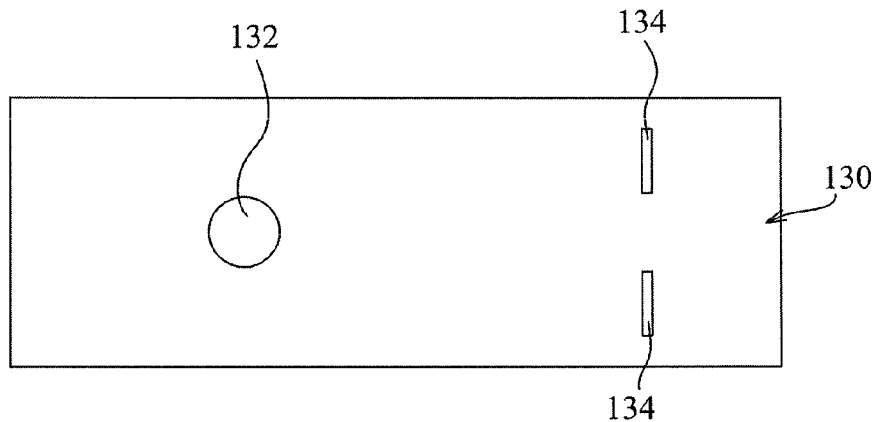
FIG. 1B illustrates an explosive view of an electrochemical blood test strip in accordance with another embodiment of the present invention.
Figure 1B:
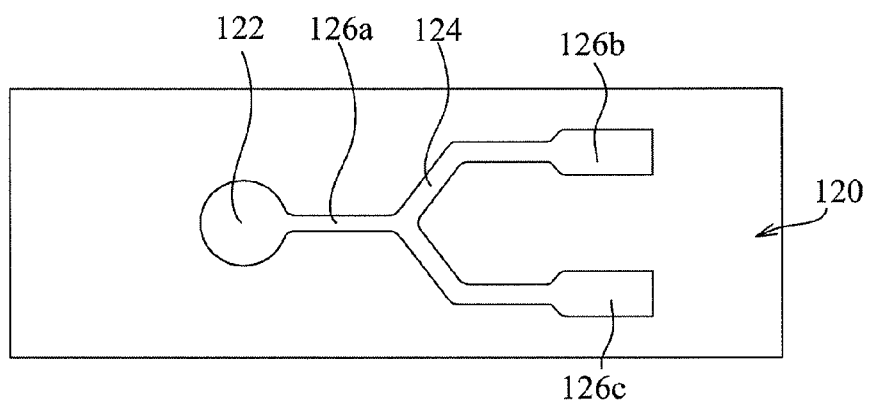
Figure 1B:
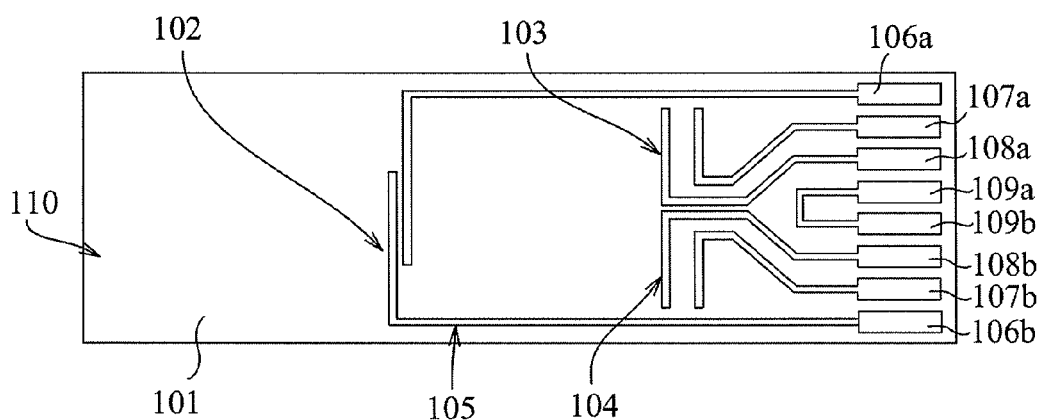

Referring to FIG. 1B, the measuring electrode pattern 105 can compose of an electrode system including a first pair of electrodes 102 positioned at the region corresponding to the reaction region 126a. The first pair of electrodes 102 extends to a first pair of contact pads 106a and 106b. A second pair of electrodes 103 positioned at the region corresponding to the reaction region 126b extends to a second pair of contact pads 107a and 108a. A third pair of electrodes 104 positioned at the region corresponding to the reaction region 126c extends to a second pair of contact pads 107b and 108b. The electrode system further includes an auto-test circuit for system extending to a fourth pair of contact pads 109a and 109b so that the electrochemical blood test strip has insertion and test functions. According to the principles of the invention, the structure is not limited to specific arrangements of the set of testing electrodes or the exact number of electrodes. Additional electrodes may be provided according to different application needs. For example, some embodiments of FIG. 1A merely include three pairs of contact pads, while other embodiments of FIG. 1B add the auto-test circuit, thus four pairs of contact pads are needed.

The separation plate 120 is depicted as including spacers interposed between the electrode plate 110 and the cover plate 130. The separation plate 120 defines the spaces of the blood sample region 122, the channel 124 and three reaction regions 126a, 126b and 126c respectively. The reaction region 126a includes a first reactive layer without containing enzyme. The reaction regions 126b and 126c include a second reactive layer (not shown) with enzyme. The reaction region 126a is used for measurement of the hemoglobin concentration and hematocrit and is used to compensate the blood concentration error. The reaction regions 126b and 126c are biochemical reaction regions. Since the enzyme can react with the blood resulting in blood clotting, the biochemical reaction regions with enzyme are used to detect the blood clotting time.

FIG. 2A schematically illustrates the blood sample region, the channel and three reaction regions of the electrochemical blood test strip in accordance with some embodiments of the present invention. In blood tests, the reaction zone 201 can be used to detect the status of blood into the reaction regions (also known as blood in). When the blood sample flows to the three reaction regions 201, 202 and 203, the three pairs of electrodes can induce the current changes, thereby confirming the status of the blood filled the three reaction regions. For example, by comparison with current variations between the reaction regions 202 and 203, whether the test data are credible can be determined. When the blood flows into the blood sample region 204, the blood is guided by the hydrophilic layer 205 into the channel and excess air is exclude by the vent holes 206.

FIG. 2B schematically illustrates the relationship between the channel width and the inflected angle of the electrochemical blood test strip in accordance with other embodiments of the invention. In some embodiments, the channel width of the blood flow can be in a range between 0.01 cm to 0.3 cm and the channel height of the blood flow can be in a range between 20 μm to 500 μm to generate capillarity effect. The width of reaction region 201 should be fixed with at least 1 mm from the front to the rear to maintain a stable blood flow, thereby making the detection of hemoglobin and hematocrit values constant. The widths of reaction region 202 and reaction region 203 can be optionally selected and designed for 1.1 to 2 times of the reaction region 201 to slow the blood flow rate and to make the blood evenly covered with the reaction regions. In FIG. 2B, the relationship between the channel widths is w2=w3, and w1:w2=1:1.1~2. The relationship between the inflected angles is d1=d2, d3=360°−(d1+d2), wherein the inflected angle d1 is greater than 90°, preferably equal to about 122.3°. The inflected angle d3 should also be greater than 90° so as to make the blood reaching the reaction region 202 and reaction region 203 at the same time due to evenly flow division force.

Further referring to FIG. 1A, the cover plate 130 is disposed on the separation plate 120. In one embodiment, the cover plate 130 includes an inlet 132 and gas vents 134, which are respectively connected to the blood sample region 122 and the reaction regions 126b and 126c. In another embodiment, a hydrophilic layer (not shown) can be optionally or alternatively formed on the lower surface of the cover plate 130 and interposed between the cover plate 130 and the separation plate 120. The hydrophilic layer can include cellulose, carboxymethyl cellulose (CMC), methyl cellulose (MC), hydroxyethyl cellulose (HEC), hydroxypropyl methyl cellulose (HPMC), acrylic, resins and salts thereof.

In blood detection, the first reaction region 126a is used for measurement of the hemoglobin concentration and hematocrit, the second and the third reaction regions 126b and 126c are biochemical reaction regions for measuring the blood clotting time. More specifically, the reaction region 126a can be individually used to detect hemoglobin or hematocrit, or to detect the hemoglobin and hematocrit simultaneously. The measured values of the hemoglobin and hematocrit can be used to compensate the error due to blood concentration.

A predetermined value is built in a diagnosis system. When the three reaction regions 126a, 126b and 126c are filled with blood, blood detection can be performed. When the blood flows from the blood sample region 122 into the reaction region 126a, the system begins with calculation (e.g., the system has built-in a predetermined time). If the blood does not arrive the reaction region 126b and 126c at a particular time, the system determines the detection (blood fill test) for failure, no more detection and operation is proceeded with. The reaction regions 126b and 126c can be also used as means for detecting the status of blood coagulation. A default parameter is built-in the diagnosis system. If the detected and calculated values from the reaction region 126b and 126c do not meet the default parameter, the system determines the blood coagulation test for failure.

From the measurement point of view, the electrochemical blood test strip of the invention includes a blood sample region for accommodating tested blood sample; a first reaction region used for detecting hemoglobin and hematocrit; a second and a third reaction regions, which are biochemical reaction regions used for detecting prothrombin time; and a channel, wherein the blood sample region is connected to the three reaction regions by the channel. The channel includes a branch such that the distance between the blood sample region and the second reaction region and the distance between the blood sample region and the third reaction region are the same.

FIG. 3 is a schematic view of an exemplary diagnostic device for measuring prothrombin time and HCT in accordance with some embodiments of the present invention. As illustrated in FIG. 3, a diagnostic device 300 using the aforementioned electrochemical blood test strip for measuring HCT and prothrombin time of a fluid includes a sensor device 320 and an electrochemical blood test strip 310 including one or more pairs of working electrodes, wherein alternating current (AC) provided by the sensor device is used to measure and calculate prothrombin time and HCT of blood test using the impedance analysis, reactance analysis, or other electrochemical analysis. The sensor device 320 includes a receiving unit 322 for accommodating the electrochemical blood test strip 310. A temperature sensor 332 is configured as means for measuring the temperature of the receiving unit 322. A temperature-maintaining unit 334 is used for controlling and maintaining temperature of the receiving unit 322 at a constant temperature. An AC generation unit 324 provides an alternating current with predetermined frequency and voltage to the electrochemical blood test strip 310. A signal-retrieving unit 328 is used to retrieve a response signal from the electrochemical blood test strip. A phase angle may be processed and calculated by a phase-angle calculation unit 326. A microprocessor 330 is used for calculating the response signal and rendering results of the HCT and the prothrombin time. A display unit 336 is used for displaying inspected results of the HCT and the prothrombin time from the microprocessor 330.

In one preferred aspect of the invention, when the blood coagulation caused by the enzyme reactions proceeds, the responding signals are received and processed by the sensor device according to the slope differences depending on the prothrombin time periods analyzed. An AC module is adopted according to the responding oscillated test signal from the electrochemical blood test strip, wherein as the blood coagulation caused by the enzyme reactions proceeds, the responding signals are received and processed by the sensor device according to the slope differences depending on the prothrombin time periods analyzed.

While the invention has been described by way of examples and in terms of preferred embodiments, it would be apparent to those skilled in the art to make various equivalent replacements, amendments and modifications in view of specification of the invention. Therefore, the scope of the appended claims should be accorded the broadest interpretation so as to encompass all such replacements, amendments and modifications without departing from the spirit and scope of the invention.

The invention claimed is:

1. An electrochemical blood test strip, comprising:
an electrode plate having circuit of measuring electrode pattern on an insulator substrate;
a separation plate disposed on the electrode plate defining a blood sample region, a channel and three reaction regions; and
a cover plate disposed on the separation plate having a blood sample inlet and vents,
wherein in measuring, a first reaction region is used for detecting hemoglobin and hematocrit and a second and a third reaction regions are biochemical reaction regions and are used for detecting prothrombin time,
wherein the blood sample region is connected to the three reaction regions by the channel, and wherein the channel includes a bifurcated branch such that the distance between the blood sample region and the second reaction region and the distance between the blood sample region and the third reaction region are the same, wherein the first reaction region is disposed between the blood sample region and the bifurcated branch, and wherein a relationship between inflected angles d1, d2 and d3 at the branch is d1=d2, and d3=360°−(d1+d2), wherein the inflected angle d1 is greater than 90°.

2. The electrochemical blood test strip as claimed in claim 1, further comprising a hydrophilic layer disposed on the bottom surface of the cover plate and between the cover plate and the separation plate.

3. The electrochemical blood test strip as claimed in claim 2, wherein the hydrophilic layer comprises cellulose, carboxymethyl cellulose (CMC), methyl cellulose (MC), hydroxyethyl cellulose (HEC), hydroxypropyl methyl cellulose (HPMC), acrylic, resins and salts thereof.

4. The electrochemical blood test strip as claimed in claim 1, wherein the measuring electrode pattern is a stacked structure comprising a metal base layer, a metal adhesive layer and a surface metal layer, wherein the metal adhesive layer is used for combining the metal base layer and the surface metal layer.

5. The electrochemical blood test strip as claimed in claim 1, wherein the electrode plate is performed with hydrophilic treatment such that hydrophilicity is created thereof.

6. The electrochemical blood test strip as claimed in claim 1, further comprising an auto-test circuit for system so that the electrochemical blood test strip have insert and test function.

7. A diagnostic device using the electrochemical blood test strip as claimed in claim 1, the diagnostic device comprises:

a test strip receiving unit for accommodating the electrochemical blood test strip;

an AC generation unit for providing an alternating current with predetermined frequency and voltage to the electrochemical blood test strip;

a signal receiving unit to retrieve a response signal from the electrochemical blood test strip;

a microprocessor for calculating the response signal and rendering results of an HCT and the prothrombin time; and a display unit for displaying inspected results of the HCT and the prothrombin time from the microprocessor.

8. The diagnostic device as claimed in claim 7, further comprising a temperature-maintaining unit for controlling and maintaining temperature of the test strip receiving unit at a constant temperature.

9. The diagnostic device as claimed in claim 7, wherein the microprocessor compares the response signal with an original AC signal, calculates a change in phase of the AC signal, and calculates the capacitance and the HCT.

10. The diagnostic device as claimed in claim 9, wherein the microprocessor further transforms the capacitance with algorithms, corrects to the prothrombin time by reference of the HCT; and calculates the prothrombin time with an international normalized ratio.

* * * * *